United States Patent [19]
Hanaoka et al.

[11] Patent Number: 4,920,150
[45] Date of Patent: Apr. 24, 1990

[54] METHOD FOR PRODUCTION OF STABILIZED SODIUM ASCORBATE POWDER

[75] Inventors: Tadashi Hanaoka, Toyonaka; Yoshimi Kondō, Kudamatsu; Ikuo Isobe, Hikari, all of Japan

[73] Assignee: Takeda Chemical Industries, Ltd., Osaka, Japan

[21] Appl. No.: 258,862

[22] Filed: Oct. 17, 1988

[30] Foreign Application Priority Data

Oct. 15, 1987 [JP] Japan ................... 62-261277

[51] Int. Cl.$^5$ .............................. A61K 31/34
[52] U.S. Cl. .................................... 514/474
[58] Field of Search ........................... 514/474

[56] References Cited

U.S. PATENT DOCUMENTS

| 2,442,461 | 6/1948 | Karrer | 167/81 |
| 3,116,204 | 12/1963 | Siegel et al. | 167/81 |
| 3,446,894 | 5/1969 | Magid | 424/176 |
| 3,493,659 | 2/1970 | Magid | 514/474 |

Primary Examiner—Douglas W. Robinson
Assistant Examiner—Raymond J. Henley, III
Attorney, Agent, or Firm—Wenderoth, Lind & Ponack

[57] ABSTRACT

According to the method for production of stabilized sodium ascorbate powder which comprises pulverizing crystals of sodium ascorbate, followed by drying at a powder temperature of 40°-80° C., sodium ascorbate powder which does not show blocking and is free from deterioration such as coloring can be obtained by drying the pulverized sodium ascorbate crystals under mild conditions.

4 Claims, No Drawings

METHOD FOR PRODUCTION OF STABILIZED SODIUM ASCORBATE POWDER

This invention relates to a method for production of sodium ascorbate powder which is stable against blocking.

Sodium ascorbate powder is generally produced by pulverization of crystals of sodium ascorbate. However the powder of sodium ascorbate thus produced is apt to show blocking during storage; for example, even when the powder is stored in a well-closed container, blocking will occur at a very high probability. This has much impaired the marketability of the powder.

Blocking of sodium ascorbate powder may be due to the water present in the powder or the moisture in the atmosphere. On this basis, blocking has been prevented so far by drying first in the presence of a dehydrating agent such as silica gel and molecular sieve followed by storing in a metallic container together with a dehydrating agent.

However with such a method to produce stabilized sodium ascorbate powder by the use of a dehydrating agent, the quality of the product has varied greatly from lot to lot and thus it has been impossible to prevent blocking of powder completely.

As a result of our research on stabilization of sodium ascorbate powder, we found that sodium ascorbate powder which is very stable against blocking can be obtained by pulverization of crystals of sodium ascorbate followed by immediate drying at a relatively low temperature of 40°–80° C. for a short time.

Namely, this invention relates to a method for production of stabilized sodium ascorbate powder which comprises pulverizing crystals of sodium ascorbate, followed by drying at a powder temperature of 40°–80° C.

Crystals of sodium ascorbate used as the starting material are usually needles or plates with loss on drying of about 50–150 ppm (110° C.×2 hours). These crystals can be pulverized by a commonly used machine for pulverization of crystals such as a cutter mill or hammer mill. It is desirable to pulverize in a stream of dry air. Sodium ascorbate powder in this invention means normally the powder of particle size of 100 mesh pass (JIS Z8801). The pulverized material is immediately dried at a powder temperature of 40°–80° C. Drying may be performed by direct heating, for example by a continuous system or batch operation system transmission heater, or by heating with warm air or hot ventilation; the aim is achieved when the powder temperature becomes 40°–80° C. Specifically, driers which may be used include those of conical, fluid-energy, or heat transmission types. Drying is usually performed in a stream of dry air but may be performed under reduced pressure. Time of drying is about 5–30 minutes. Drying at a temperature of not more than 40° C. even for a long time will be insufficient for desired prevention of blocking. Drying at temperatures higher than 80° C. will give rise to troubles of deterioration of the product such as coloring of powder. In this invention the desirable temperature of drying is in the range of 50°–60° C.

According to the method of this invention, sodium ascorbate powder which does not show blocking and is free from deterioration such as coloring can be obtained by drying the pulverized sodium ascorbate crystals under mild conditions; thus the method is industrially very useful.

This invention will be illustrated more specifically by the following examples.

EXAMPLE 1

Crystals of sodium ascorbate recrystallized from water (loss on drying: 100 ppm) were pulverized by a screen mill (manufactured by Hosokawa Micron Corp.), to give powder of 200 mesh pass. The powder was divided into 3 parts; each part was transferred to a dish and heated in a thermostat drier (inner temperature set at 120° C.). When the powder temperature reached 50° C., 60° C., or 70° C., each dish was taken out and thus 3 kinds of sodium ascorbate powder dried under different conditions were obtained.

These dried powder samples were kept still in a desiccator at 25° C. (relative humidity: 50%) and found to be very stable because blocking was not observed even after 3 months. It took 10 minutes for the powder temperature to reach 50° C. It took 15 and 20 minutes to reach 60° C. and 70° C., respectively.

EXAMPLE 2

One kg of sodium ascorbate crystals of the same lot as used in Example 1 was pulverized with hammer mill (manufactured by Nara Machinery Co., Ltd.) to give powder of 200 mesh pass. The powder was immediately dried under reduced pressure (10 Torr) at a powder temperature of 50° C. for 30 minutes in a conical drier (manufactured by Kobe Steel, Ltd.).

The powder thus treated was kept in a desiccator at 25° C. (relative humidity: 50%) and found to be very stable because blocking was not observed even after 3 months.

EXAMPLE 3

Sodium ascorbate crystals (loss on drying: 100 ppm) were pulverized with hammer mill (manufactured by Nara Machinery Co., Ltd.) to give powder of 200 mesh pass. The powder was immediately dried by ventilation with dry air heated to 60° C. into the flow of the powder for 30 minutes and thus stabilized sodium ascorbate powder was obtained. The powder was kept in a desiccator at 25° C. (relative humidity: 50%) and blocking was not observed even after 3 months. In Examples 1–3, the powder temperature was measured by a thermometer set in the powder.

COMPARATIVE EXAMPLE 1

The pulverized product of 200 mesh pass obtained in Example 1 was kept in a desiccator at 25° C. (relative humidity: 50%) without further treatment, and blocking was observed after 2 days.

COMPARATIVE EXAMPLE 2

The pulverized product of 200 mesh pass obtained in Example 1 was dried in a thermostat drier for 6 hours (the temperature inside the drier was set at 30° C.). The dried powder was kept in a desiccator under the same condition as in Comparative Example 1, and blocking was observed after 3 days.

COMPARATIVE EXAMPLE 3

The pulverized product of 200 mesh pass obtained in Example 1 was dried at room temperature (20°–25° C.) under reduced pressure (10 Torr) for 20 hours. The dried powder showed blocking after 5 days in a desiccator under the same condition as in Comparative Example 1.

What we claim is:

1. A method for production of stabilized sodium ascorbate powder, which comprises pulverizing crystals of sodium ascorbate, immediately followed by drying said crystals to a powder temperature of 40°–80° C.

2. The method according to claim 1 wherein the time of drying is about 5 to 30 minutes.

3. The method according to claim 1 wherein the powder temperature is in the range of 50°–60° C.

4. The method according to claim 1 wherein the particle size of stabilized sodium ascorbate powder is 100 mesh pass.

* * * * *